US00PP14358P39

(12) United States Plant Patent
Bessho

(10) Patent No.: US PP14,358 P3
(45) Date of Patent: Dec. 9, 2003

(54) CALIBRACHOA PLANT NAMED 'KAKEGAWA S49'

(50) Latin Name: *Calibrachoa spp.*
Varietal Denomination: Kakegawa

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 10/058,848

(22) Filed: Jan. 30, 2002

(65) Prior Publication Data

US 2003/0145363 P1 Jul. 31, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Jondle & Associates P.C.

(57) ABSTRACT

'Kakegawa S49' is a new variety of Calibrachoa. This new variety has light purple violet colored flowers and dark green foliage.

1 Drawing Sheet

BACKGROUND OF THE INVENTION

Figure 1:
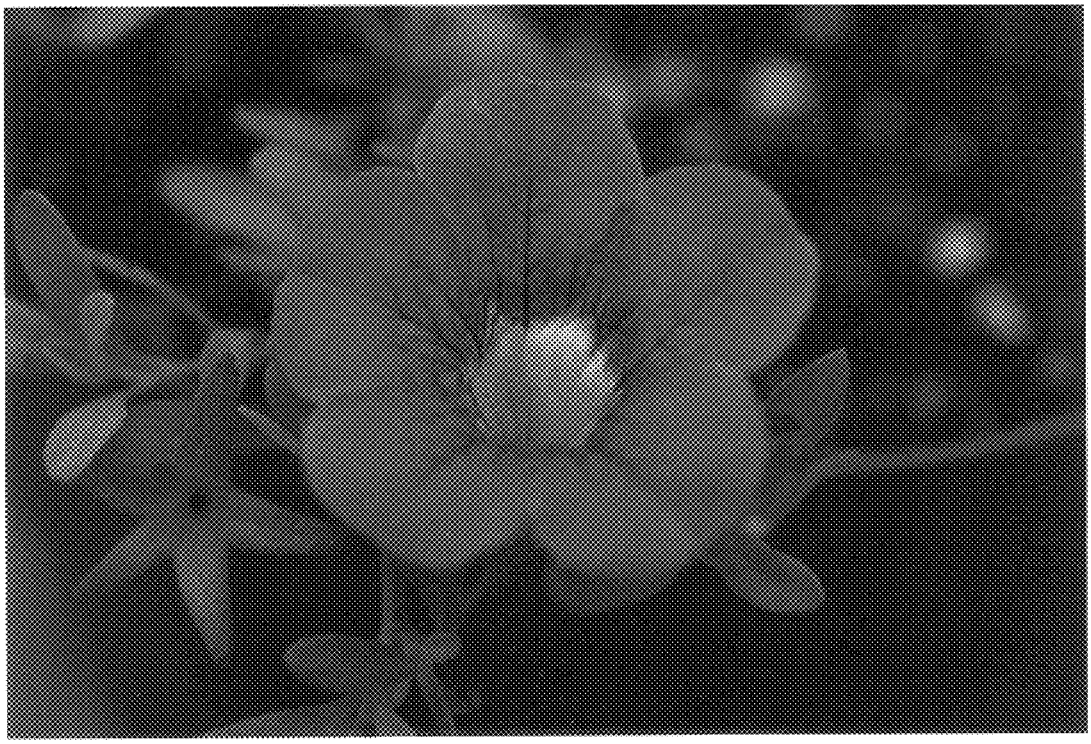
Figure 2:
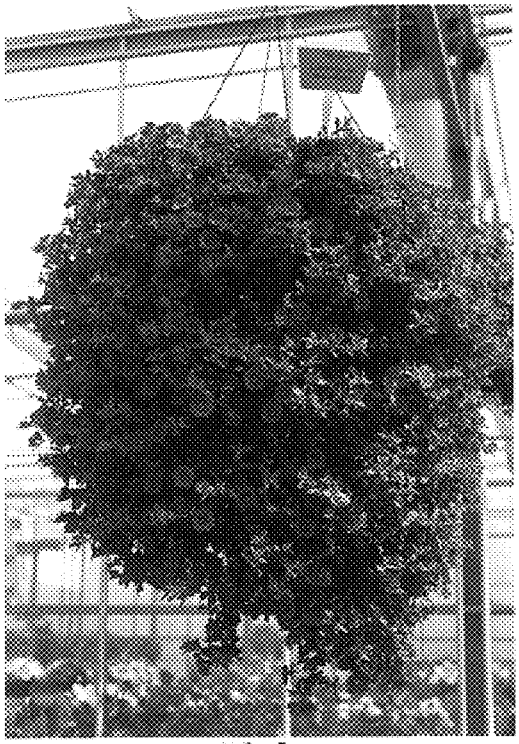

'Kakegawa S49' originated from a hybridization made in spring 1996 in Kakegawa, Japan. The female parent was the commercial variety 'Liricashower Rose' (U.S. Plant Pat. No. 9,884). The male parent was the commercial variety 'Million Bells Trailing White' (U.S. Plant Pat. No. 10,278). Seed from this cross was sown in spring 1997 and four $F_1$ plants were selected. The four selections were intercrossed and the resulting seed bulked together to produce $F_2$ seed. The $F_2$ seed was sown in summer 1997 and two plants were selected for having sky blue flower color. The selections were intercrossed and the resulting seed bulked together to produce $F_3$ seed. In spring 1998 the $F_3$ seed was sown and one plant, designated as line K9-119, was selected. This line was vegetatively propagated in Salinas, Calif. in summer 1998 and again in spring 1999. In these two vegetative generations the line was evaluated and determined that the traits are firmly fixed and stable. No inherent variation or off-types have been identified.

DESCRIPTION OF THE GENUS CALIBRACHOA LLAVE & LEX

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of several species classified as Petunia. These studies discovered that P. hybrida and its ancestrial species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The base of the cuttings were dipped for 1 to 2 seconds in a 1:9 solution of Dip 'N Grow (1 part solution to 9 parts water) root inducing solution immediately prior to sticking into the cell trays. Cuttings were put into plastic cell trays having 98 cells, and containing a peat moss-based growing medium. The cuttings were misted with water from overhead for 10 seconds every 30 minutes until sufficient roots were formed. The vegetative cuttings were propagated in five to six weeks.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24C.

DETAILED DESCRIPTION OF THE NEW PLANT

The following traits and characteristics describe the new variety. The observed plants were 3 moths old from a rooted cutting.

Classification:
- *Family.*—Solanaceae.
- *Species.*—Calibrachoa spp.
- *Common names.*—Petunia.

Parentage: 'Kakegawa S49' is a third generation selection from mass selection and intercrossing of progeny from the hybridization of 'Liricashower Rose' (U.S. Plant Pat. No. 9,884) and the variety 'Million Bells Trailing White' (U.S. Plant Pat. No. 10,278).

Growth:
- *Habit.*—Decumbent, mounding in center.
- *Height.*—23.0 cm.
- *Spread.*—115.0 cm when grown in a 41 cm hanging basket or pot, and using five 20 cm potted plants in one hanging basket.
- *Life cycle.*—Annual.
- *Time to produce a rooted cutting.*—3 weeks.
- *Time to bloom from propagation.*—10 weeks.
- *Form.*—Branching, dense.

Stems:
- *Stem color.*—R.H.S. 144B (yellow - green).
- *Anthocyanin color.*—R.H.S. N77A (purple).
- *Pubescence.*—Slightly.
- *Pubescence color.*—R.H.S. 155D (white).
- *Pubescence shape.*—Pointed.
- *Stem description.*—Round, ancipital.
- *Stem diameter.*—2.0 mm.
- *Internode length.*—1.5 to 2.5 cm.

Leaves:
- *Leaf tip.*—Mucronate.
- *Leaf arragement.*—Alternate.
- *Leaf base.*—Decurrent.
- *Leaf color.*—Upper surface: R.H.S. 137A (green); lower surface: R.H.S. 138B (green).
- *Leaf frangrance.*—Absent.
- *Leaf margin.*—Entire.
- *Leaf surface.*—Slightly.
- *Petiole color.*—R.H.S. 138C (green).
- *Petiole length.*—2.0 to 3.0 mm.
- *Leaf length.*—3.0 to 3.5 cm.
- *Leaf shape.*—Elliptical.
- *Leaf width.*—1.0 cm at full expansion.

Flowers:
- *Calyx.*—5 sepals; 1.0×3.0 cm (l×w); free.
- *Corolla.*—5 petals, fused.
- *Flower diameter.*—3.0 cm.
- *Bud color.*—R.H.S. N144D (yellow-green).
- *Bud shape.*—Ovate.
- *Bud surface.*—Pubescent.
- *Duration of flower life.*—5 days.
- *Flowering habit.*—Indeterminate.
- *Ovary.*—Superior.
- *Placenta arrangement.*—Central.
- *Peduncle.*—2.5 cm length; 1.0 mm diameter; slightly smooth, short pubescence.
- *Inflorescence type.*—Solitary.
- *Stamens.*—5 stamens, three short and two long, free.
- *Stamens color.*—R.H.S. 144D (yellow-green).
- *Stigma color.*—R.H.S. 134A (green).
- *Style color.*—R.H.S. 144D (yellow-green).
- *Petal size.*—2.5×1.5 cm (l×w).
- *Petal color.*—Upper surface: R.H.S. N82B (purple-violet); lower surface: R.H.S. 84D (violet); corolla throat: R.H.S. 155D (white) with R.H.S. N77A (purple) veins; corolla tube: inner surface: R.H.S. 4C (yellow); outer surface: R.H.S. 4C (yellow).
- *Petal pubescence.*—Glabrous.
- *Pollen color.*—R.H.S. 1A (green-yellow).
- *Produces seed.*—No.

COMPARISON WITH MOST SIMILAR VARIETY

'Kakegawa S49' is most similar to the variety 'Colorburst Violet' (U.S. Plant Pat. No. 12,086). 'Kakegawa S49' differs from 'Colorburst Violet' in that it has a lighter purple-violet flower color, a pale yellow corolla throat and a more prostrate, trailing plant habit. Shown below in Table one are comparisons with the parental cultivar.

TABLE 1

| | |
|---|---|
| Parents | Liricashower Rose & Million Bells Trailing White |
| Plant Habit | Female and male decumbent; S49 decumbent and mounding in center |
| Flower Color | Female purplish rose: male white: S49 light violet |
| Flower Size (diameter) | Female and S49 are 2.5–3.0 cm: male 2.6–2.8 cm |
| Stem Pubescence | Female and S49 slight: male is moderate |
| Stem Thickness | Female 1.0–1.5 mm (laterals); male 1.2 mm: S49 2.0 mm |
| Leaf Color (upper) | Female grayish green (RHS 137B): male deep yellow green (RHS 146A): S49 grayish green (RHS 137A) |
| Leaf Pubescence | Female, male and S49 is slight |
| Leaf Shape | Female slightly oblanceolate: male is lanceolate: S49 is elliptical |

PLANT DISEASE AND PEST RESISTANCE

Excellent resistance to rain, heat and drought. Will not tolerate temperatures below 10C. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepitopdera.

What is claimed is:

1. A new and distinct Calibrachoa plant as shown and described herein.

* * * * *